(12) United States Patent
Mikkaichi et al.

(10) Patent No.: US 7,875,041 B2
(45) Date of Patent: Jan. 25, 2011

(54) SUTURING METHOD FOR PENETRATING HOLE

(75) Inventors: Takayasu Mikkaichi, Tokyo (JP); Masayuki Iwasaka, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 271 days.

(21) Appl. No.: 11/238,019

(22) Filed: Sep. 28, 2005

(65) Prior Publication Data

US 2007/0073322 A1      Mar. 29, 2007

(51) Int. Cl.
*A61B 17/04* (2006.01)
(52) U.S. Cl. ...................... 606/144; 606/232
(58) Field of Classification Search ............ 606/144, 606/145, 146, 147, 148, 149, 232
See application file for complete search history.

(56) References Cited

U.S. PATENT DOCUMENTS

| | | | | |
|---|---|---|---|---|
| 5,222,508 A * | 6/1993 | Contarini | ............ | 128/898 |
| 5,336,239 A * | 8/1994 | Gimpelson | ............ | 606/223 |
| 5,391,182 A * | 2/1995 | Chin | ............ | 606/213 |
| 5,507,754 A * | 4/1996 | Green et al. | ............ | 606/139 |
| 5,601,571 A * | 2/1997 | Moss | ............ | 606/139 |
| 5,810,848 A * | 9/1998 | Hayhurst | ............ | 606/144 |
| 6,066,146 A | 5/2000 | Carroll et al. | | |
| 6,203,554 B1 * | 3/2001 | Roberts | ............ | 606/144 |
| 6,398,796 B2 * | 6/2002 | Levinson | ............ | 606/144 |
| 6,500,184 B1 * | 12/2002 | Chan et al. | ............ | 606/144 |
| 6,535,764 B2 * | 3/2003 | Imran et al. | ............ | 607/40 |
| 6,966,916 B2 * | 11/2005 | Kumar | ............ | 606/144 |
| 2003/0216613 A1 * | 11/2003 | Suzuki et al. | ............ | 600/104 |
| 2003/0236535 A1 * | 12/2003 | Onuki et al. | ............ | 606/144 |

* cited by examiner

*Primary Examiner*—(Jackie) Tan-Uyen T Ho
*Assistant Examiner*—Jing Rui Ou
(74) *Attorney, Agent, or Firm*—Scully, Scott, Murphy & Presser, P.C.

(57) ABSTRACT

A suturing method for a penetrating hole formed in a luminal organ using a suture material to close the penetrating hole according to the present invention includes the steps of inserting a needle at a position that is removed from the open edge of the penetrating hole by a distance that is less than the thickness of the wall of the luminal organ and passing the needle through the wall; sending out from the needle an anchor affixed to the end of the suture material; placing the anchor in place by pulling the needle through the wall and passing the suture material through the wall; and tightening the suture material after passing the suture material in the same direction through the wall at multiple sites interposing the penetrating hole.

8 Claims, 10 Drawing Sheets

SUTURING METHOD FOR PENETRATING HOLE

BACKGROUND OF THE INVENTION

1. Field of the Invention

The present invention relates to a suturing method that employs an endoscope. For example, the present invention relates to a method for suturing a penetrating hole that is formed in the wall of a luminal organ.

2. Description of Related Art

When a procedure is to be carried out inside the body of a patient, the procedure may be performed by surgically incising the patient's body, or via oral or rectal endoscopy. Procedures employing endoscopy are performed by passing forceps, high-frequency surgical instruments, dissecting instruments, suturing instruments and the like through channels in the endoscope. For example, in the case where a medical procedure is to be carried out inside the abdominal cavity using an endoscope inserted into the lumen of an organ via one of the body's natural orifices, such as the mouth or rectum, a hole is formed by resecting or dissecting tissue from inside the abdominal cavity. The medical procedure is then carried out by approaching the abdominal cavity from the lumen via this hole. After the procedure has been performed, suturing instruments are employed to close the hole that was formed.

SUMMARY OF THE INVENTION

A suturing method for a penetrating hole according to the present invention comprises the steps of: inserting a needle at a position that is removed from the open edges of the penetrating hole by a distance that is less than the thickness of the wall of the luminal organ, and passing the needle through the wall; sending out from the needle an anchor affixed to the end of the suture material; placing the anchor in place by pulling the needle through the wall and passing the suture material through the wall; and tightening the suture material after passing the suturing material in the same direction through the wall at multiple sites interposing the penetrating hole.

DETAILED DESCRIPTION OF THE PREFERRED EMBODIMENT

Figure 1:
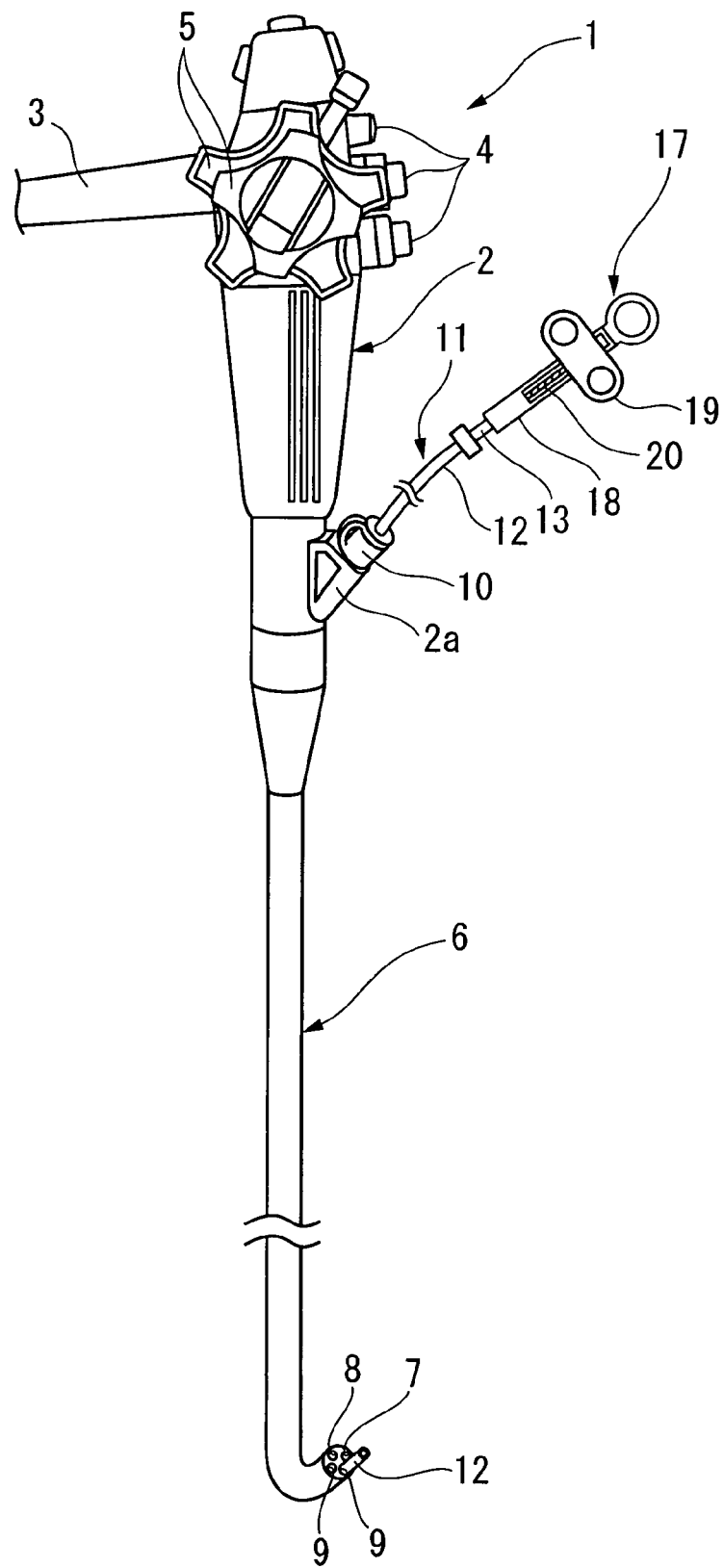
FIG. 1 is a diagram showing the schematic structure of an endoscope and suturing device.

The endoscope and suturing device employed in a present embodiment are shown in FIG. 1. An endoscope 1 (flexible endoscope) has an endoscope control section 2 which is manipulated by the operator. The endoscope control section 2 is connected to a control device by a universal cable 3, and is provided with a variety of switches 4 and angle knobs 5. A flexible, long endoscope insertion section 6 is provided extending from the end of the endoscope control section 2. An observation device 7, for capturing images within the body, an illuminating device 8, and the end openings of channels 9 are provided at the end of the endoscope insertion section 6. An image capturing device provided with a CCD (Charge Coupled Device), an optical fiber and the like, are employed in the observation device 7. The illuminating device 8 has an optical fiber for guiding light from a light source. The channels 9 pass through the endoscope insertion section 6 and open on the side portion 2a of the endoscope control section 2. A cover 10 is attached to an opening of the side portion 2a. An insertion hole is formed on the cover 10, through which treatment instruments, such as a suturing device 11, or observation devices, are inserted into the channel 9.

Figure 2:
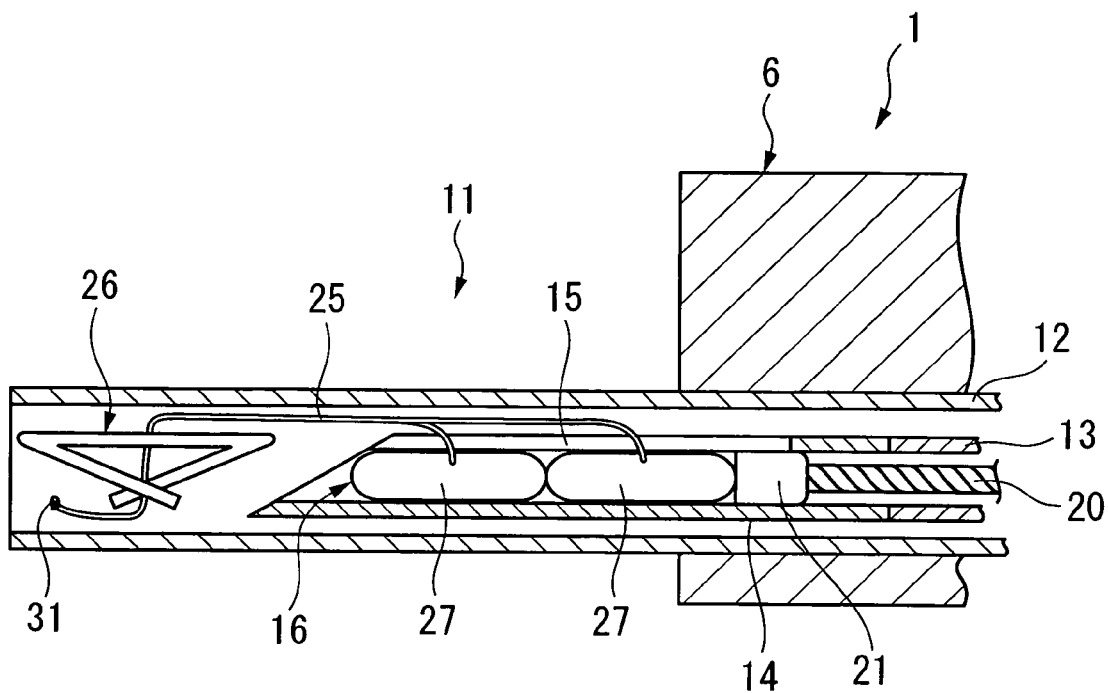
FIG. 2 is a cross-sectional view of the end portion of the suturing device and endoscope.
Figure 3:
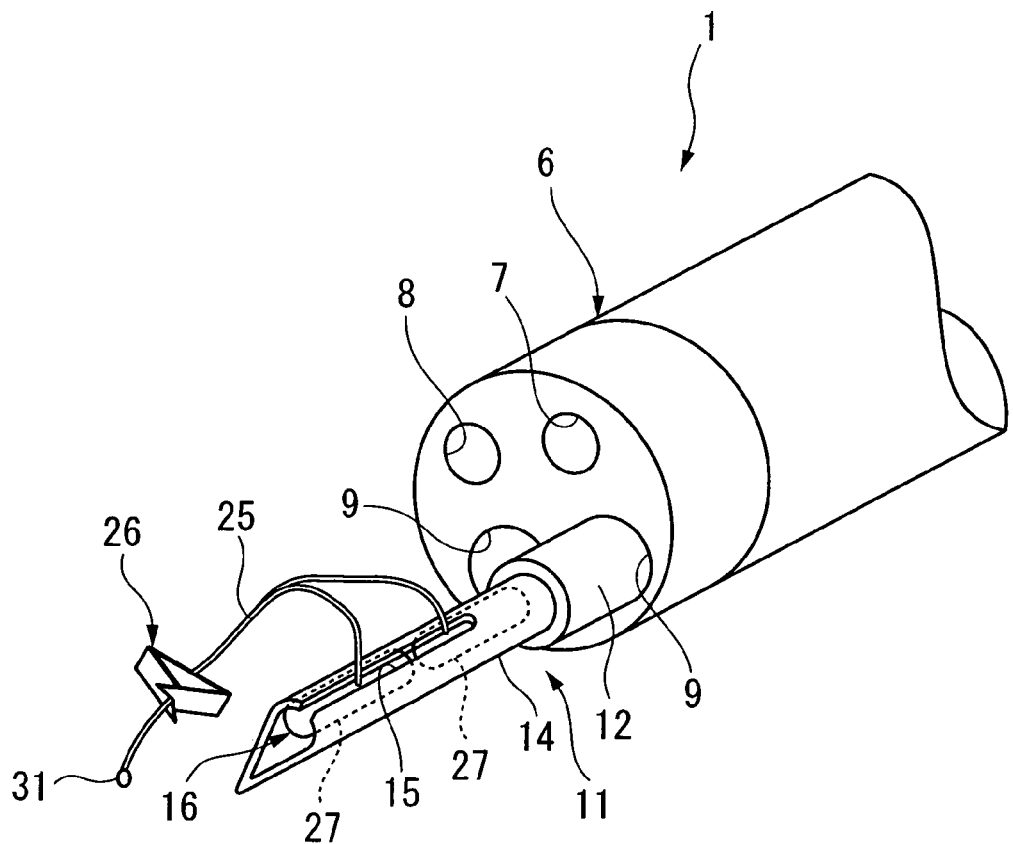
FIG. 3 is a perspective view of the end portion of the suturing device and endoscope.

As shown in FIGS. 1 through 3, the suturing device 11 is designed such that a flexible inner sheath 13 can pass within a flexible outer sheath 12 in a freely advancing and retracting manner. A needle 14 is affixed to the end of the inner sheath 13. A slit 15 extends in the longitudinal direction from the end of the needle 14. A suturing instrument 16 is housed inside the needle 14. The lengths of the outer sheath 12 and the inner sheath 13, respectively, are greater than the length of the channel 9 of the endoscope 1. A control section 17 is attached to the base of the inner sheath 13. The control section 17 has a handle 19 that is freely sliding with respect to a control section main body 18. The base of a pusher 20 is fixed in place to the handle 19. The pusher 20 passes though the inside of the inner sheath 13 and extends to the needle 14. The end 21 of the pusher 20 comes into contact with the suturing instrument 16.

Figure 4:
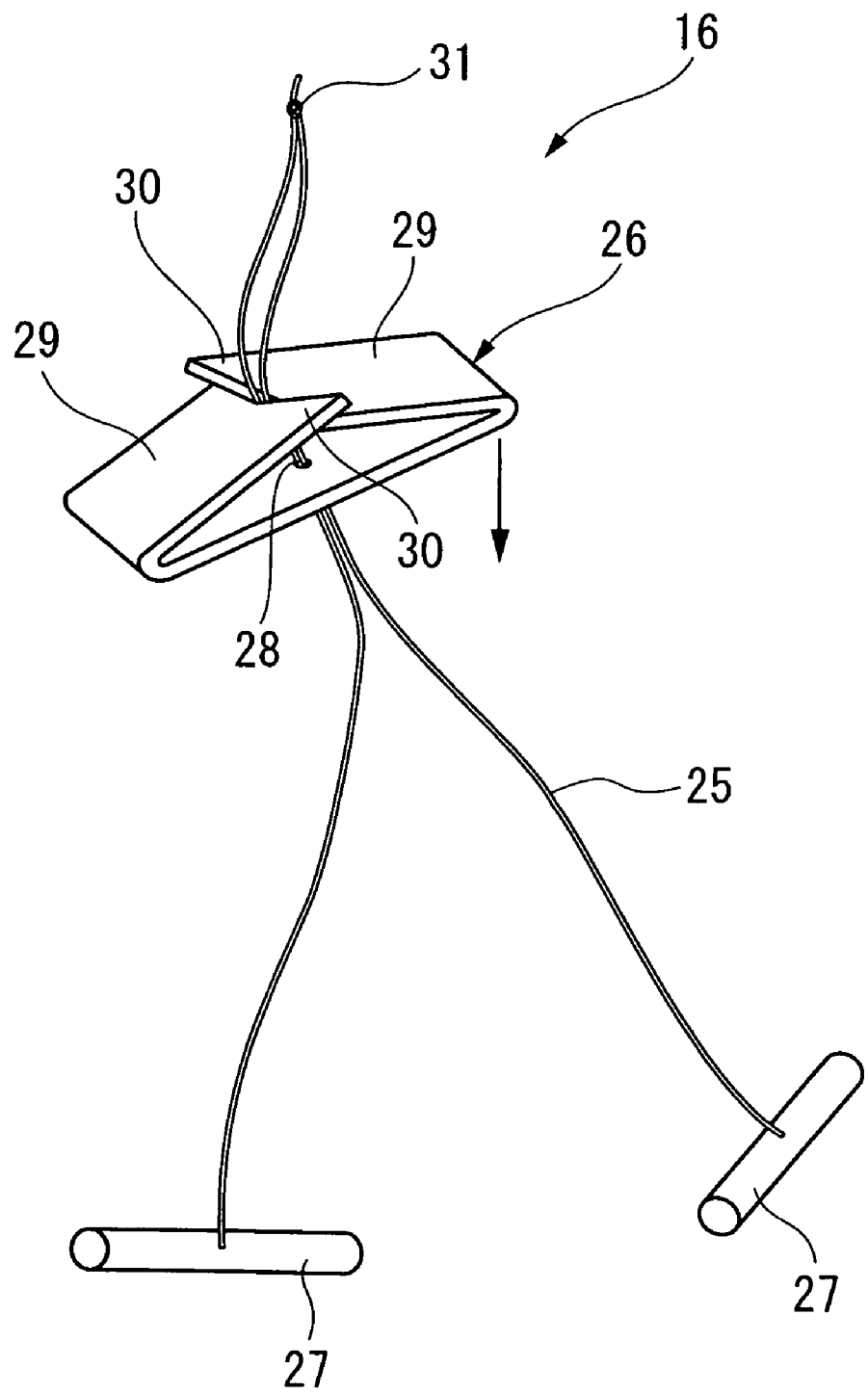
FIG. 4 is a diagram showing the structure of the suturing instrument.

As shown in FIG. 4, the suturing instrument 16 is provided with suture material 25. The suture material 25 is folded over approximately in half, and has a knot 31 provided near the folding back point. The suture material 25, with the ends thereof bundled together, is passed through a stopper 26, which is approximately triangular in shape. Respective anchors 27 are affixed to each end of the suture material 25. The anchor 27 has a columnar shape, and the suture material 25 is fixed in place at a position that is substantially in the center of the longitudinal direction of the anchor 27. The stopper 26 has a hole 28 at the center of the longitudinal direction of its long narrow plate member through which the suture material 25 is passed. The ends 29 in the longitudinal direction of the stopper 26 are bent back diagonally, thereby gripping the suture material 25. The ends 29 in the longitudinal direction of the stopper 26 are cut into triangularly shaped cut pieces 30. By bending the back ends 29 diagonally so that the cut pieces 30 intersect, the suture material 25 is gripped by the stopper 26. As a result, the suture material 25 does not fall out from between the ends 29. Further, if the knot 31 of the suture material 25 is pulled in a direction moving away from the stopper 26, the ends 29 of the stopper 26 open slightly. Accordingly, the stopper 26 permits movement of the suture material 25 in this direction. On the other hand, when the end of the suture material 25 is pulled from the anchor 27 side, then the suture material 25 begins to move in the direction indicated by the arrow in FIG. 4. However, in this case, the ends 29 of the stopper 26 close, tightening on the suture material 25, so that the suture material 25 does not move.

As shown in FIG. 3, the two anchors 27 of the suturing instrument 16 are sequentially housed in internal holes in the needle 14. The suture material 25 is pulled out from the slit 15 of the needle 14. As shown in FIG. 2, the stopper 26 is housed further toward the tip of the outer sheath 12 than the needle 14. Note that the number of the anchors 27 and the shape of the stopper 26 are not limited to the embodiment shown in the figures.

Next, the suturing method according to this embodiment will be explained with reference to FIGS. 5 through 15. Note that FIGS. 5 through 12 are schematic views for explaining technique, and employ the stomach as an example of a luminal organ.

Figure 5:
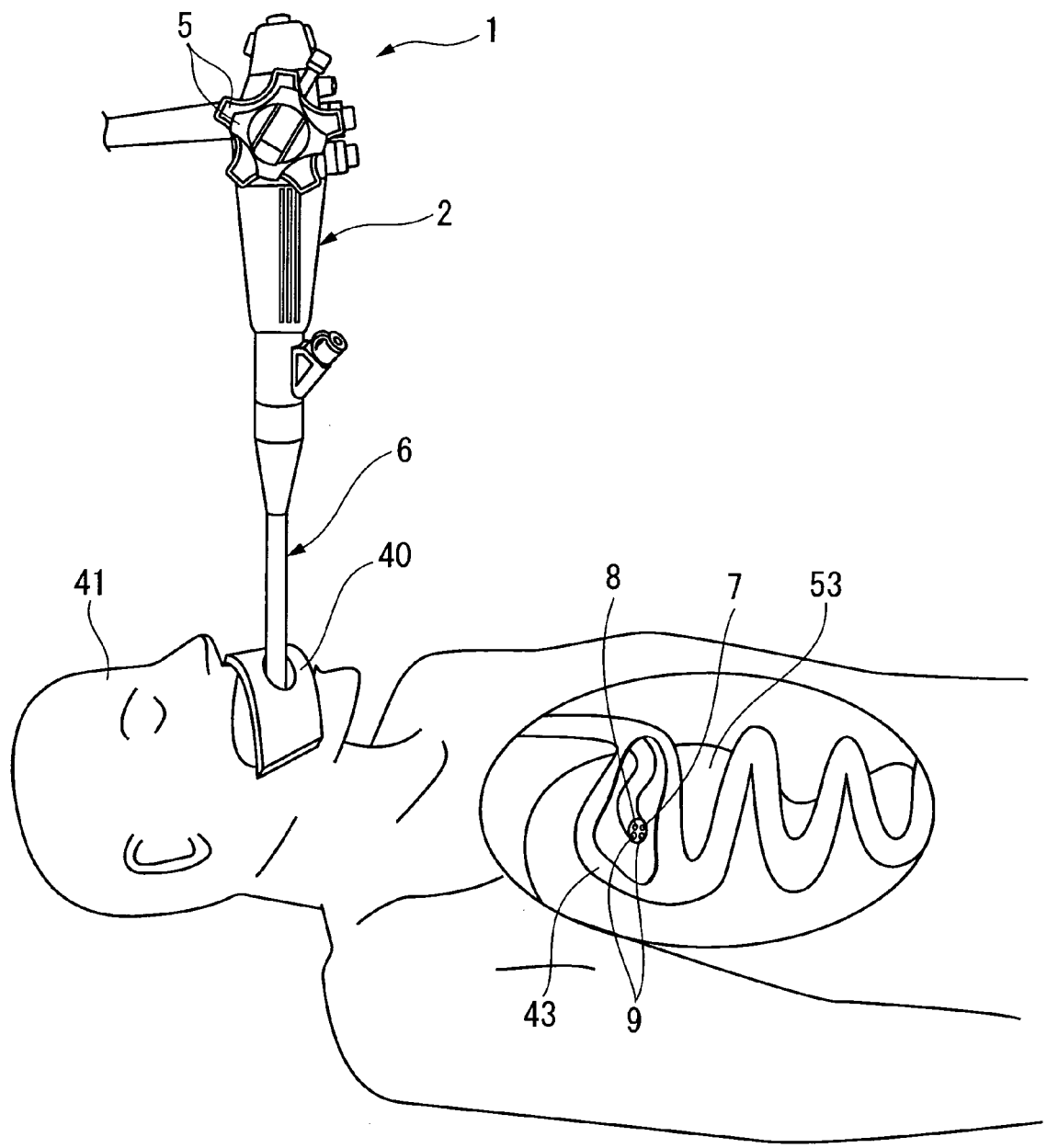
FIG. 5 is a diagram showing the step for inserting the endoscope into the patient's stomach and visualizing the area to be incised from within the stomach.
Figure 6:
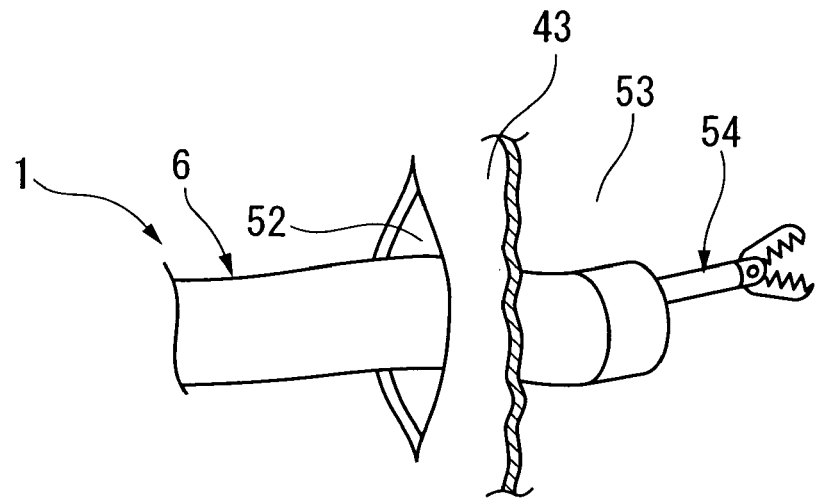
FIG. 6 is a diagram showing the step for carrying out a procedure inside the abdominal cavity by passing the instrument through a penetrating hole

As shown in FIG. 5, the endoscope insertion section 6 is inserted via the oral cavity (or other such natural orifice of the body as the anus, nose, ears, etc.) of a patient 41, who has been equipped with a mouthpiece 40. The end of the endoscope insertion section 6 is bent using the angle knob 5. A needle-shaped knife, which is a high frequency resecting instrument, is passed into the channel 9 of the endoscope insertion section 6, and is used to form a penetrating hole by incising the tissue in the wall of his stomach 43. As shown in FIG. 6, the endoscope insertion section 6 is passed through a penetrating hole 52 formed in the stomach 43 and is guided into abdominal cavity 53. Forceps 54 are passed through the channel 9 and are employed to carry out the procedure in abdominal cavity 53. Once the procedure is completed, the endoscope insertion section 6 is withdrawn from the stomach 43.

Figure 7:
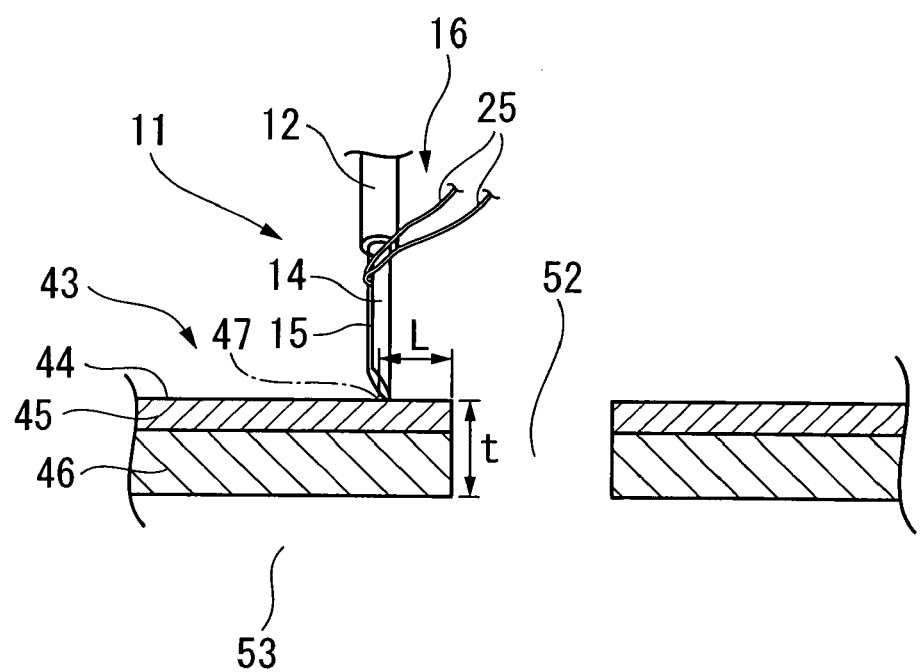
FIG. 7 is a diagram showing the position for inserting the needle.

When suturing together the penetrating hole 52, the suturing device 11 is passed through the channel 9 of the endoscope insertion section 6, and the needle 14 of the suturing device 11 is pushed out from the outer sheath 12. At this time, the stopper 26 falls into the stomach 43. The suturing device 11 is advanced forward with respect to the endoscope 1, and the needle 14 is inserted substantially perpendicularly into the tissue around the penetrating hole 52, passing from the inside (the mucosa 45 side) to the outside (the abdominal cavity 53 side) of the stomach 43. As shown in FIG. 7, an insertion position 47 is located at a length L away from the open edge of the penetrating hole 52. The length L is smaller than the thickness t of a wall 44 of the stomach 43. Note that the wall 44 is comprised of a mucosa 45 on the inside and a muscular tunic 46 on the outside.

Figure 8:
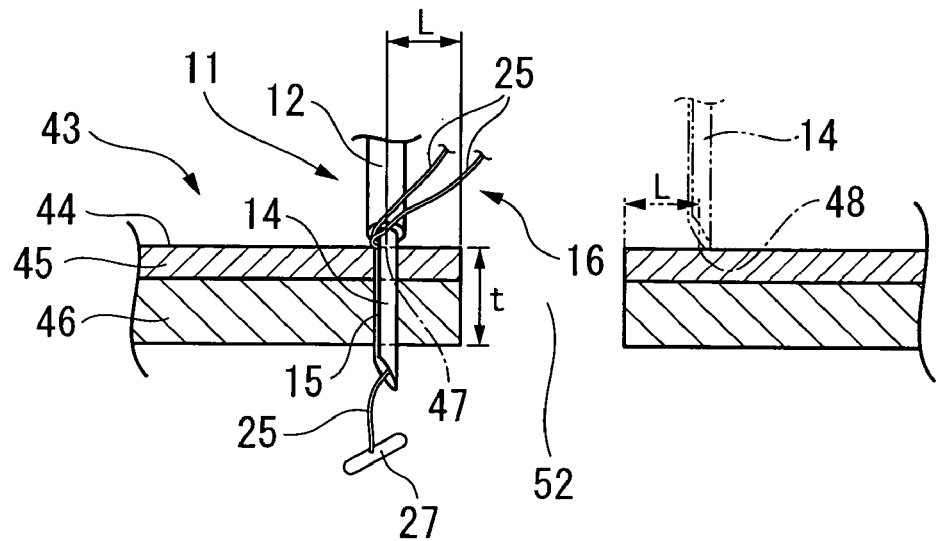
FIG. 8 is a diagram in which the anchor has been pushed out after the needle has pierced and passed through the wall of the organ.
Figure 9:
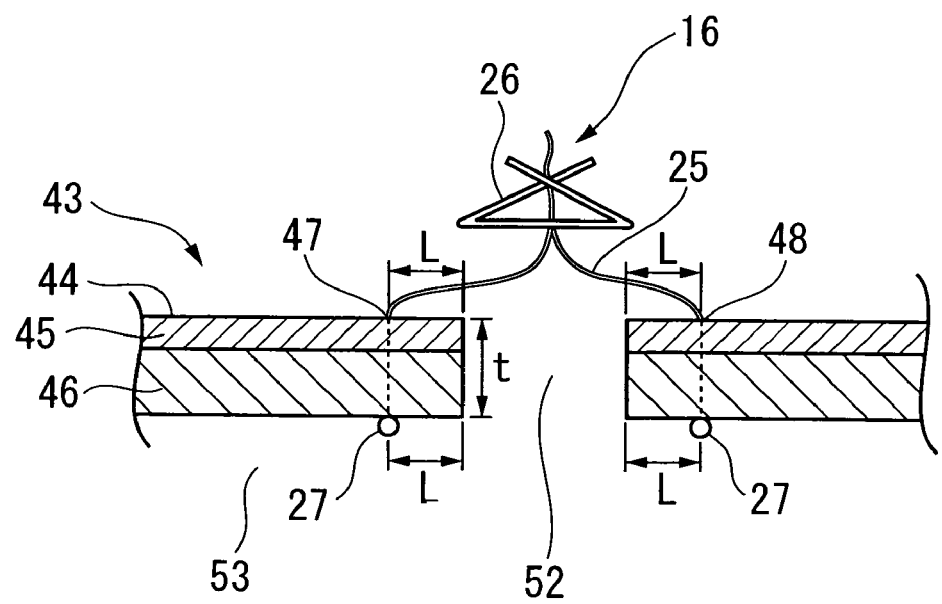
FIG. 9 is a diagram in which the suturing instrument is attached.

The suturing device 11 is advanced forward until the needle 14 passes through the tissue of the wall 44. The handle 19 (see FIG. 1) of the control section 17 is manipulated to advance the pusher 20 forward. As shown in FIG. 8, one anchor 27 is pushed out into the abdominal cavity 53. Once the one anchor 27 is pushed out, the needle 14 is pulled out from the wall 44. One anchor 27 is thus retained in abdominal cavity 53, and the suture material 25 passes through the wall 44. Next, the needle 14 is again inserted substantially perpendicular to the tissue at a substantially symmetrical position with respect to the insertion position 47, with the penetrating hole 52 interposed therebetween. The needle 14 is inserted from the inside (mucosa 45 side) to the outside (abdominal cavity 53 side) of the stomach 43. The insertion position 48 of the needle 14 is located at a length L from the open edge of the penetrating hole 52, as indicated by the imaginary line in FIG. 8. When the needle 14 passes though the wall 44, the second anchor 27 is pushed out on the abdominal cavity 53 side, and the needle 14 is withdrawn. The suture material 25 passes substantially perpendicularly through the wall 44. As shown in FIG. 9, in the suturing instrument 16, the two anchors 27 are each retained at positions that are, respectively, the length L from the open edge of the penetrating hole 52.

Figure 10:
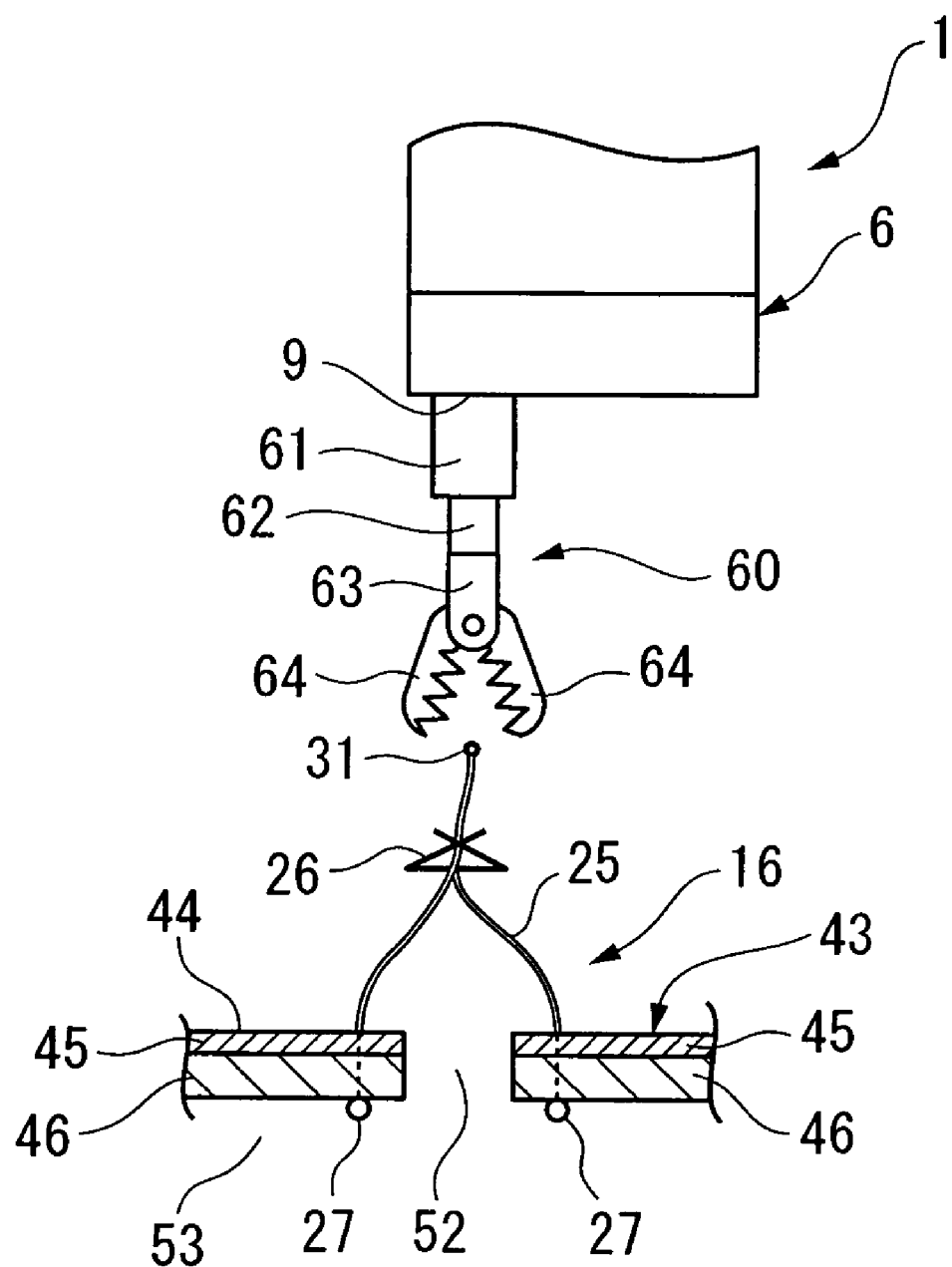
FIG. 10 is a diagram showing the forceps for tightening the suturing instrument.

The suturing instrument 16 is tightened using forceps 60 as shown in FIG. 10, for example. The forceps 60 possess an outer sheath 61 that has an external diameter that is larger than the anchor 27. An inner sheath 62 passes through the inside of an outer sheath 61 in a freely advancing and retracting manner. A support member 63 is present at the end of the inner sheath 62. A pair of gripping pieces 64 are supported by this support member 63 to enable opening and closing thereof.

Figure 11:
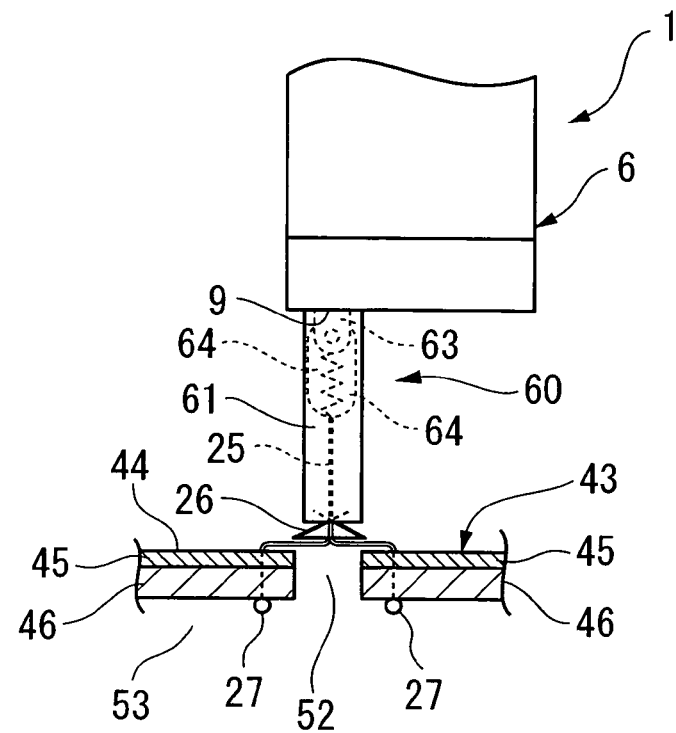
FIG. 11 is a diagram showing the step for tightening the suturing instrument using the outer sheath of the forceps.

The knot 31 of the suture material 25 of the suture instrument 16 is gripped by the gripping pieces 64, after which the outer sheath 61 is advanced forward, so that the end of the outer sheath 61 comes into contact with the stopper 26. As shown in FIG. 11, when the outer sheath 61 is further advanced, the stopper 26 is pushed into the wall 44 of the stomach 43. Since it is designed to enable movement in this direction, the stopper 26 moves toward the wall 44. Since the position of the pair of the gripping pieces 64 does not change, the stopper 26 advances relative to the suture material 25. The distance between the stopper 26 and the anchors 27 is thereby decreased and the suture material 25 is tightened. As a result, the tissue surrounding penetrating hole 52 is drawn together and penetrating hole 52 is sutured closed by the suture material 25.

Figure 12:
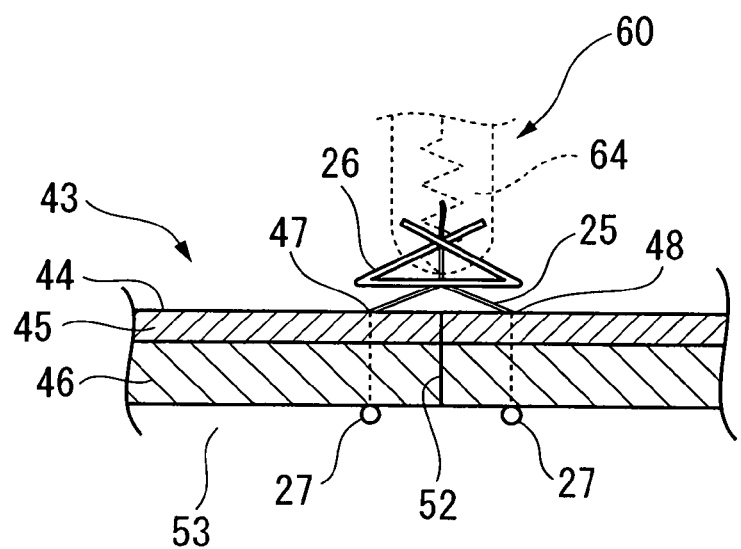
FIG. 12 is a diagram showing the state in which the penetrating hole has been closed through the process of tightening the suturing instrument.
Figure 13:
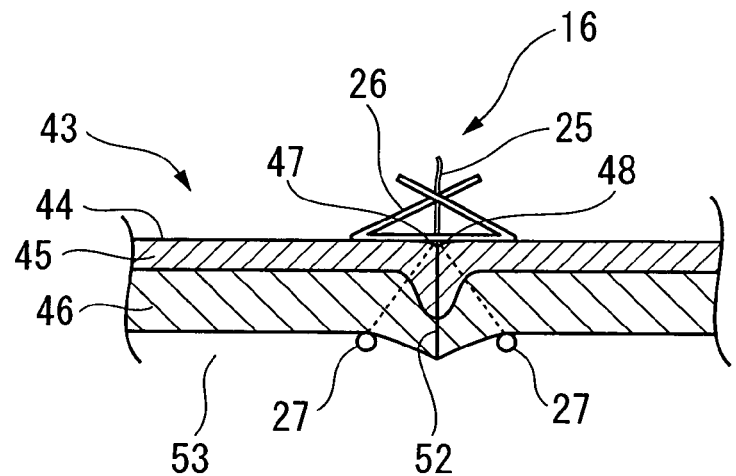
FIG. 13 is a diagram in which the insertion positions are substantially apposed by tightening the suturing instrument.

As shown in FIG. 12, the surfaces of the inner periphery of the penetrating hole 52 are adhered closely together. If the suture material 25 is further tightened, then, as shown in FIG. 13, the insertion positions 47, 48 are drawn together so as to be substantially apposed. Since the length L is smaller than the thickness t of the wall 44, the tissue near the insertion positions 47, 48 is compressed and partially crushed, and a state in which the surfaces of the inner periphery of the penetrating hole 52 are adhered closely together is maintained. Specifically, the mucosa 45 surfaces adhere closely together, and the muscular tunic 46 surfaces adhere closely together.

Once the penetrating hole 52 has been sutured using the suturing instrument 16, the outer sheath 61 is retracted, the gripping pieces 64 open, and the forceps 60 release the suture material 25. While movement of the ends of the stopper 26 is possible in the direction which tightens the tissue with the suture material 25, the stopper 26 ends work to tighten the suture material 25 in the direction in which the suture material 25 relaxes. Accordingly, even if the suturing instrument 16 is retained inside the stomach 43, the suture material 25 does not slacken.

In this embodiment, the insertion positions 47, 48 for the needle 14 were set according to the thickness of the wall 44. As a result, the penetrating hole can be sutured with greater surety irrespective of the type of luminal organ. Since the insertion positions 47, 48 are located a length L from the open edges of the penetrating hole 52, and this length L is smaller than the thickness t of the wall 44 which is to be sutured, it becomes possible to adhere the muscular tunics 46 with even greater surety. Since the muscular tunics 46 adhere together more readily then the mucosa 45, closing up of the penetrating hole 52 proceeds quickly, resulting in faster healing.

Figure 14:
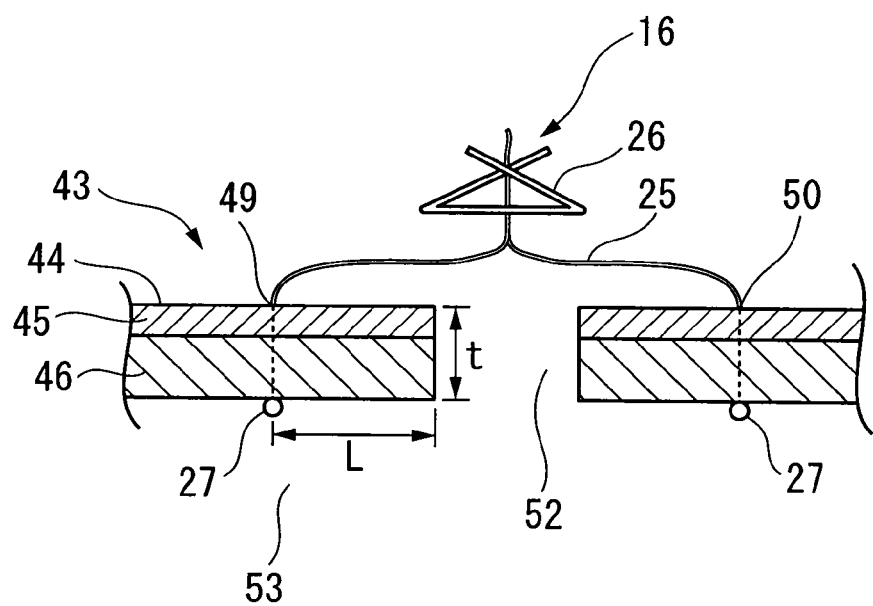
FIG. 14 is a diagram for explaining the case where the positions of insertion exceed the thickness of the wall.
Figure 15:
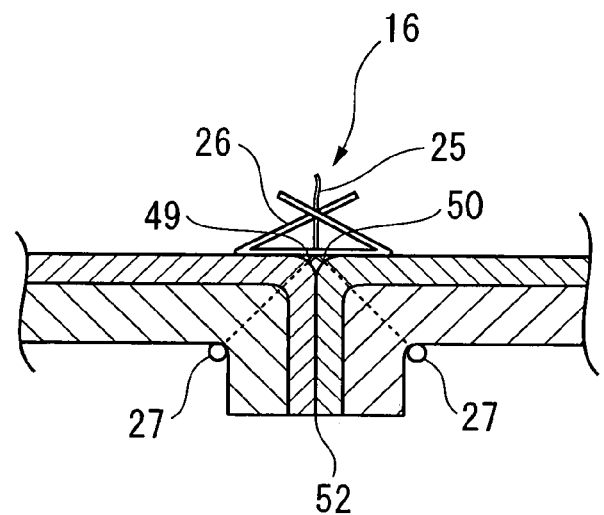
FIG. 15 is a diagram in which the insertion positions are substantially apposed by tightening the suturing instrument, for the case where the positions of exertion exceed the thickness of the wall.

Note that when suturing an opening in the abdominal wall, because the abdominal wall is thick, it will adhere together easily simply by tightening with the suture material. In the case of digestive organs such as the stomach 34, however, the wall 44 is thin, so that suturing is difficult due to the softness of the tissue. In particular, in the case where the endoscope 1 is employed, since the suturing is carried out from the mucosa 45 side, it was difficult for the tissues to adhere together using conventional suturing methods. For example, as shown in FIG. 14, when the length L from the penetrating hole 52 to the insertion positions 49, 50 is greater than the thickness t of the wall 44, the insertion positions 49, 50 approach one another when the suture material 25 is tightened. Since the tissue between the insertion positions 49, 50 is long, these tissues become everted as shown in FIG. 15. As a result, the respective mucosa 45 adheres tightly together, but the muscular tunics 46 cease to be in contact with one another. It is typically said that the mucosa 45 does not readily adhere together. Accordingly, if suturing such that only respective mucosa 45 is apposed is performed, it becomes difficult for the penetrating hole 52 to close. This type of problem is resolved in the present embodiment.

Note that the present invention is not limited to the various embodiments disclosed above, but can be employed in a broad range of applications.

For example, the suture material 25 was passed though the wall 44 by passing from the inside to the outside of the stomach 43. However, it is also acceptable to pass the suture material 25 through the wall 44 by passing it from the outside to the inside of the stomach 43. In this case, the suturing device 11 is passed through the penetrating hole 52 and relayed out to the abdominal cavity 53 side. The needle 14 is inserted into the wall 44 from the abdominal cavity 53 side. The insertion point is at length L from the open edge of the penetrating hole 52. Once the suture material 25 has passed through the wall in the same direction, interposed about the penetrating hole 52, and the two anchors 27 are each retained inside the stomach 43, the stopper 26 is pulled into the stomach 43, and the suturing instrument 16 is tightened. When the suturing instrument 16 is tightened such that the insertion points are apposed, the penetrating hole 52 is sutured together in a state such that the respective muscular tunics are closely adhered.

Figure 16:
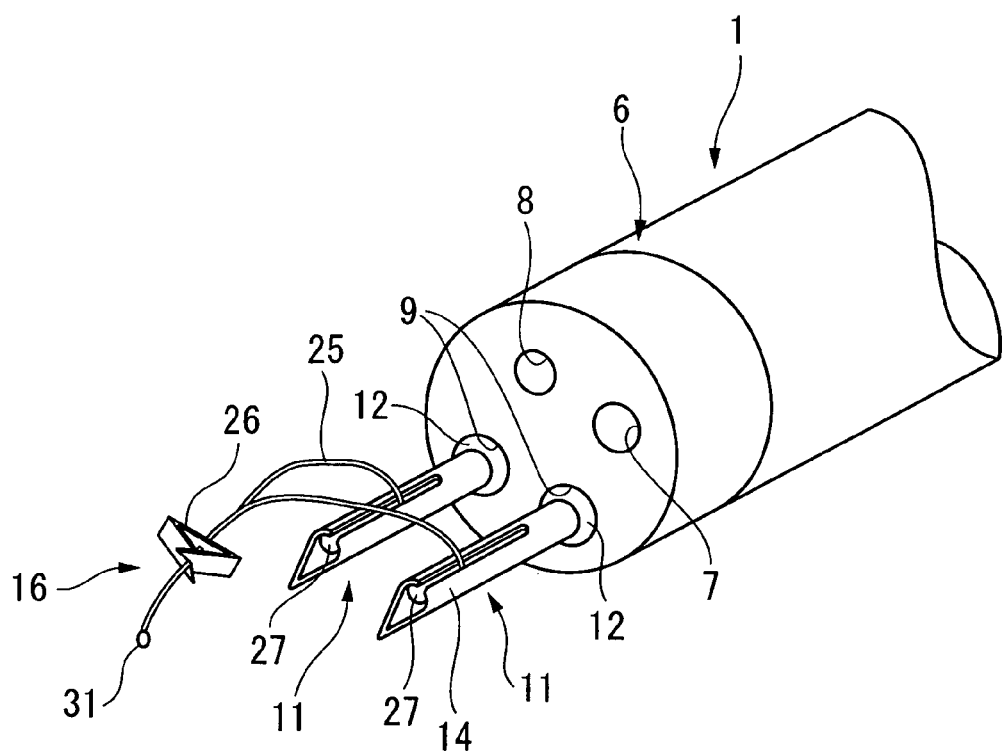
FIG. 16 is a diagram in which two suturing devices are inserted in parallel into the insertion section of an endoscope.

In the case where the endoscope insertion section 6 has two channels 9 as shown in FIG. 16, one suturing device 11 each can be passed through the channels 9. In this case, an anchor 27 may be housed in the respective needles 14 of each suturing device 11.

What is claimed is:

1. A suturing method for a penetrating hole formed in a stomach using a suture material passing through a hole of a stopper to close the penetrating hole comprising the steps of:
    inserting a needle at insertion positions that are separated from an open edge of said penetrating hole by a distance that is less than a thickness of a wall of said stomach from a mucosa side of said stomach, and passing said needle through said wall;
    sending out from said needle an anchor affixed to an end of the suture material;
    placing said anchor in place by pulling said needle through said wall and passing said suture material through said wall;
    adhering muscular tunics of said stomach together by tightening said suture material so that said stopper and said stomach contact with each other and all of the insertion positions and the hole of said stopper approximately coincide with each other by advancing said stopper relative to said suture material so that a distance between said stopper and said anchor is decreased after passing said suture material in the same direction through said wall at multiple sites interposing said penetrating hole.

2. A suturing method for a penetrating hole according to claim 1 further comprising the step of tightening said suture material further so that the tissue near the insertion position is compressed and partially crushed.

3. A suturing method for a penetrating hole according to claim 1, wherein said stopper only moves in a direction in which the distance between said stopper and said anchor is decreased.

4. A suturing method for a penetrating hole according to claim 1 further comprising the step of falling said stopper into the mucosa side of said stomach.

5. A suturing method for a penetrating hole according to claim 1, wherein the step of adhering the muscular tunics of said stomach is conducted so that said wall from the open edge of said penetrating hole to each of the insertion positions is bent toward a side of an abdominal cavity of said stomach.

6. A suturing method for a penetrating hole according to claim 1, wherein said stopper and the mucosa side of said stomach contact with each other by advancing said stopper.

7. A suturing method for a penetrating hole according to claim 1, wherein a plate member of said stopper and said stomach contact with each other by advancing said stopper, the plate member having the hole of said stopper.

8. A suturing method for a penetrating hole according to claim 7, wherein substantially all of a surface of the plate member and said stomach contact with each other by advancing said stopper.

* * * * *